United States Patent [19]
Falcone

[11] Patent Number: 5,464,012
[45] Date of Patent: Nov. 7, 1995

[54] PATIENT ALARM DETECTION USING TARGET MODE

[75] Inventor: Ronald Falcone, Hudson, N.H.

[73] Assignee: Hewlett-Packard Company, Palo Alto, Calif.

[21] Appl. No.: 120,490

[22] Filed: Sep. 13, 1993

[51] Int. Cl.$^6$ ........................................ A61B 5/00
[52] U.S. Cl. .................... 128/630; 128/633; 128/672; 128/736; 128/696; 128/716; 128/668; 128/748
[58] Field of Search ............................ 128/630, 632–635, 128/637, 664–673, 677–698, 700–730, 736, 748; 364/411.02–413.05; 340/573

[56] References Cited

U.S. PATENT DOCUMENTS

| | | | |
|---|---|---|---|
| 4,788,983 | 12/1988 | Brink et al. | 128/706 |
| 4,860,763 | 8/1989 | Schminke | 128/707 |
| 5,002,055 | 3/1991 | Merki et al. | 128/635 |
| 5,007,430 | 4/1991 | Dardik | 128/707 |
| 5,297,558 | 3/1994 | Acorn et al. | 128/700 |

OTHER PUBLICATIONS

J. H. Philip, "Thoughtful Alarms" in J. S. Gravenstein et al, eds., Essential Noninvasive Monitoring in Anesthesia, 1980, pp. 191–201.

J. H. Philip, "Overview: Creating Practical Alarms for the Future", 1989.

J. E. W. Beneken et al, "Accuracy in Trend Detection", in J. S. Gravenstein et al, eds., An Integrated Approach to Monitoring, 1983, pp. 134–135.

*Primary Examiner*—Angela D. Sykes
*Assistant Examiner*—Robert L. Nasser, Jr.

[57] ABSTRACT

A method and apparatus for detecting an alarm in a patient monitoring system during the transient period which occurs after performing a procedure that intentionally alters the patient's state. The patient monitoring system executes the steps of initiating a target mode when the user sets target limits of a physiological parameter, establishing dynamic limits that vary with time, comparing measured parameter values with the dynamic limits, and generating an alarm when any of the measured parameter values falls outside the dynamic limits. The target mode is terminated when any of the measured parameter values falls within the target limits. The dynamic limits ensure that the physiological parameter is monitored during the transient period after an intervention procedure, without generating false alarms.

8 Claims, 4 Drawing Sheets

PATIENT ALARM DETECTION USING TARGET MODE

FIELD OF THE INVENTION

This invention relates to medical monitoring of patients and, more particularly, to improved methods and apparatus for alarm detection when a patient's state is intentionally altered.

BACKGROUND OF THE INVENTION

Patient monitoring systems are commonly used for monitoring the condition of a patient, such as in coronary care units and intensive care units of a hospital. Such systems typically include a bedside monitor having one or more sensors, such as ECG sensors, blood pressure sensors and temperature sensors, attached to the patient. The sensors measure various physiological parameters of the patient. The measured parameters are processed by a system processor. The processed information may be displayed on a video display screen and stored for later analysis. Patient physiological information from several bedside monitors may be forwarded to a central station located, for example, at a nursing station.

The bedside patient monitor and the central station may display physiological parameters as waveforms and/or numerical values. Another important function of patient monitoring systems is to generate alarms when one or more of the physiological parameters indicates that the patient requires attention. Such alarms are necessary because it is not feasible for the display screen of the patient monitoring system to be observed continuously. Alarms are typically annunciated both visibly and audibly.

The conventional way of specifying alarm criteria is to set a fixed upper threshold and a fixed lower threshold for a measurement, such as heart rate. When the measured value goes above the upper threshold or below the lower threshold, an alarm is generated. This approach does not accommodate the situation where a clinician intentionally alters the state of a patient, such as by administering an anesthetic or a drug. Such intervention may cause the patient's heart rate, blood pressure and other physiological parameters to go outside the fixed alarm limits and to generate an alarm, even though these changes are expected and normal. Many clinicians turn off or disable alarms because they become annoyed with a patient monitor that generates an alarm when they intentionally alter a patient's state as described above. When the alarm is turned off, the clinician has the responsibility for monitoring the patient's condition continuously during the intervention process. This may lead to inadequate monitoring. If the clinician resets the alarm limits to the steady state parameter values that are desired after intervention, the patient monitor will generate an alarm immediately, because the parameter values have not yet reached the final values defined by the new alarm limits.

Various, more sophisticated alarm criteria have been proposed. See, for example, J. H. Philip, "Thoughtful Alarms", in J. S. Gravenstein et al, eds. *Essential Noninvasive Monitoring in Anesthesia*, 1980, page 191–201, and J. H. Philip, "Overview: Creating Practical Alarms for the Future", 1989. Such approaches may be unnecessarily complex for relatively straightforward patient monitoring requirements and do not address alarm detection when a patient's state is intentionally altered.

SUMMARY OF THE INVENTION

According to a first aspect of the invention, a method for detecting a patient alarm is provided. The method is used in a patient monitoring system that includes at least one sensor for measuring values of a physiological parameter and a processor for processing the measured parameter values and for providing information representative of the measured parameter values. In accordance with the invention, the patient monitoring system executes steps comprising setting target limits of the physiological parameter in response to user selections, initiating a target mode after setting of the target limits, establishing dynamic limits of the physiological parameter that vary with time, comparing measured parameter values with the dynamic limits, and generating a alarm when any of the measured parameter values falls outside the dynamic limits, until any of the measured parameter values falls within the target limits.

The dynamic limits are typically established so as to converge on the target limits as a function of time. The dynamic limits are preferably initiated at the time when an intervention procedure is begun. Preferably, the target mode is terminated when any of the measured parameter values falls within the target limits. After the target mode is terminated, an alarm is generated when any of the measured parameter values is outside the target limits. The target mode can be reinitiated by a user after an alarm is generated.

According to another aspect of the invention, a patient monitoring system comprises a sensor for measuring values of a physiological parameter and a processor for processing the measured parameter values. The processor comprises means for setting target limits of the physiological parameter in response to user selections, means for initiating a target mode after setting of the target limits, means for establishing dynamic limits of the physiological parameter that vary with time, means for comparing measured parameter values with the dynamic limits, and means for generating an alarm when any of the measured parameter values falls outside the dynamic limits, until any of the measured parameter values falls within the target limits.

BRIEF DESCRIPTION OF THE DRAWINGS

For a better understanding of the present invention, reference is made to the accompanying drawings, which are incorporated herein by reference and in which.

DETAILED DESCRIPTION

Figure 1:
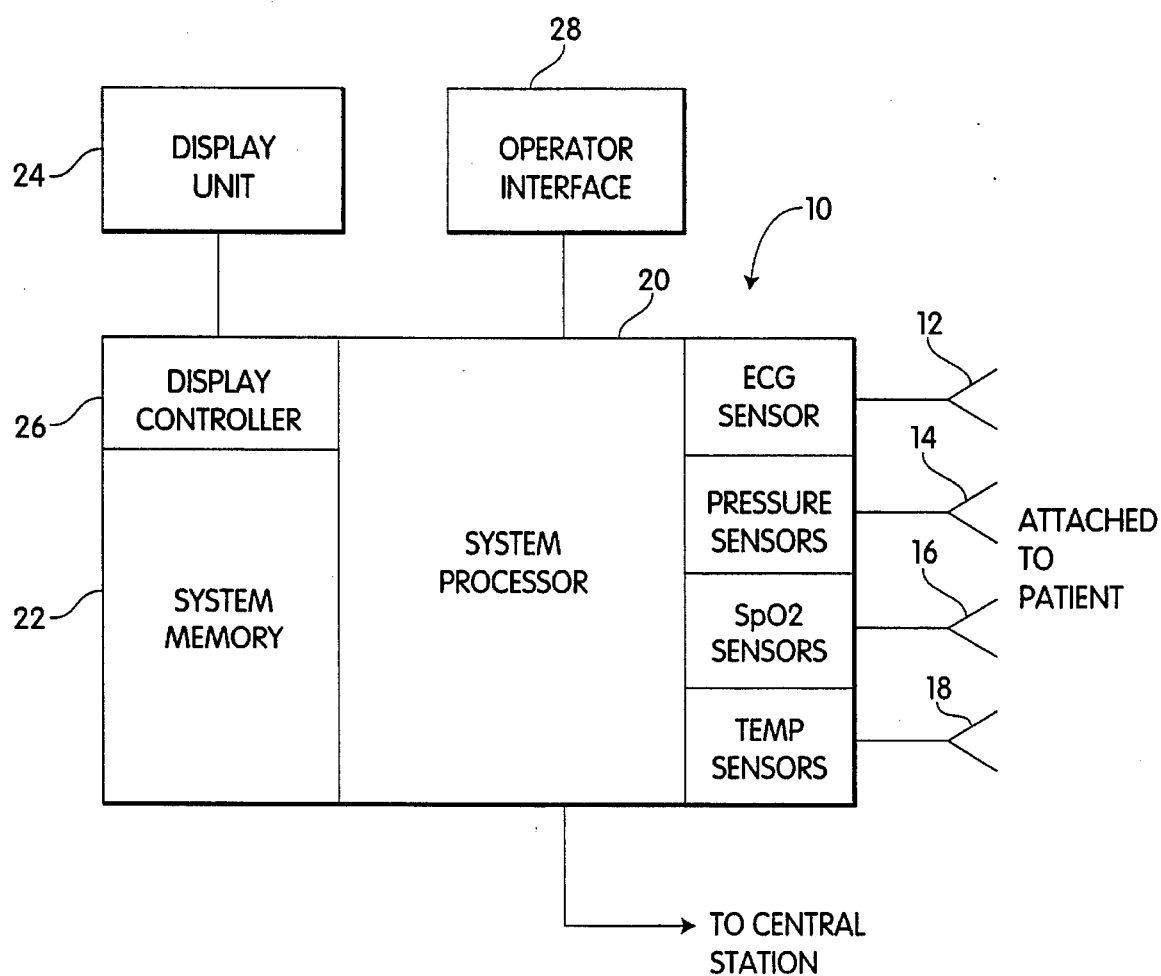
FIG. 1 is a block diagram of a patient monitoring system suitable for incorporation of the present invention.

A block diagram of a patient monitoring system suitable for incorporation of the alarm detection technique of the present invention is shown in FIG. 1. A bedside monitor 10 is typically located at a patient's bedside and includes one or more transducers, or sensors, attached to the patient. The transducers may include ECG sensors 12, pressure sensors 14, SpO$_2$ sensors 16 and temperature sensors 18. The number and type of sensors is optional. The sensors sense various physiological parameters of interest.

The physiological parameter measurements obtained by the sensors are supplied to a system processor 20. Typically, analog sensor output signals are amplified and are converted to digital data by an analog-to-digital converter (not shown). The digital data representing the sensor signals is supplied to the system processor 20. The system processor 20 operates in conjunction with a system memory 22, a display unit 24, typically a video display screen, a display controller 26 and an operator interface 28 to monitor the patient's condition and to supply information to a user. The system processor 20 may, for example, include a Motorola 680X0 microprocessor.

The information presented on the display unit 24 may include waveforms of one or more physiological parameters, numerical values of one or more physiological parameters and alarms which indicate that the patient requires attention. Typically, alarms are also annunciated audibly. The physiological parameter information obtained by the sensors can be stored in a system memory 22 for subsequent analysis. Information regarding the patient's condition can also be supplied to a central station. An example of a bedside monitor of the type shown in FIG. 1 is the Model M1176A, manufactured and sold by Hewlett-Packard Company.

Figure 2:
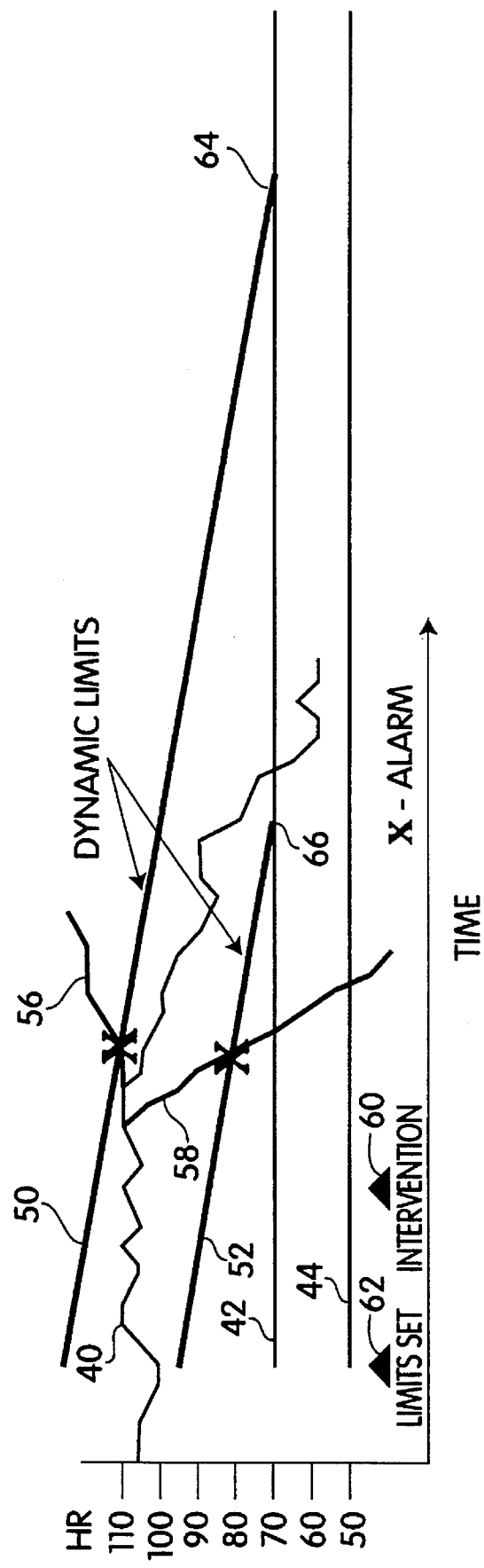
FIG. 2 is a graph of heart rate as a function of time, showing target limits and dynamic limits utilized in accordance with the present invention.

A technique for alarm detection in accordance with the present invention is illustrated with reference to FIG. 2. In FIG. 2, heart rate is plotted as a function of time. However, it will be understood that the present invention can be applied to any physiological parameter which may be of interest in connection with an intervention procedure. The present invention applies in the case of intervention procedures where a patient's state, or condition, is intentionally altered by a clinician. Examples include altering a patient's condition by administering an anesthetic or other drug. However, the present invention applies to any procedure or intervention where a patient's physiological parameters are intentionally altered.

In the example of FIG. 2, the patient's heart rate as a function time is plotted as curve 40. Initially, the patient's heart rate is a range of about 100 to 110. As a result of an intervention procedure, for example, administering a drug, it is expected that the patient's heart rate will decrease over a specified period of time to a range of about 50 to 70. Both the magnitude of the change and the time required for the change are important factors in determining whether the patient has reacted normally or abnormally to the intervention.

In prior art systems, the clinician could either turn off or disable the alarm associated with the heart rate or other parameter being measured, during the transition period between intervention and the final, steady state condition of the patient. Also, the clinician could set very widely spaced alarm limits and thereby effectively disable the alarm. Either case required the clinician to monitor the patient's parameters continuously during a potentially critical period and was not satisfactory.

In accordance with the invention, the clinician sets target limits for each physiological parameter that is expected to be altered as a result of the intervention procedure. The physiological parameter can be a directly measured parameter or one that is calculated from one or more measured values. Examples of calculated parameters include heart rate and cardiac index. The target limits establish upper and lower bounds on the acceptable range for the steady state value of the physiological parameter after the intervention procedure. In FIG. 2, upper target limit 42 and lower target limit 44 are shown. When the clinician sets new target limits 42 and 44, the system processor 20 establishes dynamic limits 50 and 52 based on the new target limits 42 and 44, the current measured value of the parameter and preprogrammed or user-entered information regarding an acceptable time for the transition between the current value and the target limits. The dynamic limits 50 and 52 establish upper and lower bounds on the parameter value during a period starting at the beginning of the intervention procedure and terminating when the parameter value is within the target limits 42 and 44.

During the transition period, the bedside monitor 10 enters a target mode in which it monitors the transient condition after the beginning of the intervention procedure. As long as the measured parameter values remain within the dynamic limits 50 and 52, no alarm is generated and the parameter value eventually falls within the target limits 42 and 44. At this time, the target mode is terminated. If the parameter value goes above dynamic limit 50, as indicated by curve 56, an alarm is immediately generated. In the example of FIG. 2, this indicates that the heart rate is increasing, rather than decreasing as expected. If the measured parameter value goes below the dynamic limit 52, as indicated by curve 58, an alarm is also generated immediately. In the example of FIG. 2, this indicates that the heart rate is decreasing more rapidly than expected and may be indicative that the patient requires attention. In either case, an alarm is generated during the transition period when the alarm would most likely have been disabled in prior art systems.

The dynamic limits 50 and 52 are shown in the example of FIG. 2 as spaced-apart straight lines having equal slopes as a function of time. In general, the dynamic limits may be arbitrary functions of time. Furthermore, the upper and lower dynamic limits may be different functions of time and may vary in spacing as a function of time. The dynamic limits may increase as a function of time where the parameter value is expected to increase after intervention. Finally, the dynamic limits may increase and then decrease, or vice-versa, as a function of time where the parameter value is expected to return to its initial value within a specified time period. In any case, the dynamic limits intersect the target limits within limited time periods and establish a time "window" within which the measured parameter values must fall within the target limits. In the example of FIG. 2, dynamic limits 50 and 52 intersect target limit 42 at points 64 and 66, respectively.

The dynamic limits are established for an intervention procedure based on an expected, normal reaction to the procedure. Important parameters of the dynamic limits are the values of the upper and lower limits as a function of time and the time required for the parameter value to fall within the target limits 42 and 44. Preferably, the dynamic limits are established based on the measured parameter value at the time of the intervention, as indicated by the arrow 60 in FIG. 2. Assuming that the intervention procedure is started shortly after the target limits are set by the clinician, as indicated by arrow 62 in FIG. 2, the dynamic limits 50 and 52 can be established when the target limits are set. Alternatively, the operator interface 28 (FIG. 1) of the bedside monitor 10 can include a key for notifying the system that the intervention procedure is beginning. When the intervention procedure is begun, the system initiates the target mode and compares the measured values of the parameter with the dynamic limits. When the measured values fall within the target limits 42 and 44, the target mode is terminated. Optionally, the system can provide an indication that the measured values fall within the target limits and that the target mode has been terminated. After the target mode is terminated, an alarm is generated at any time when the measured parameter value goes outside the target limits 42 and 44.

As a further option, the target mode can be reinitiated by the user after an alarm is generated during the target mode, if the clinician determines that the patient's condition is satisfactory. When the target mode is reinitiated, the target limits remain the same but the dynamic limits are recomputed based on the current measured value of the physiological parameter.

Figure 3A:
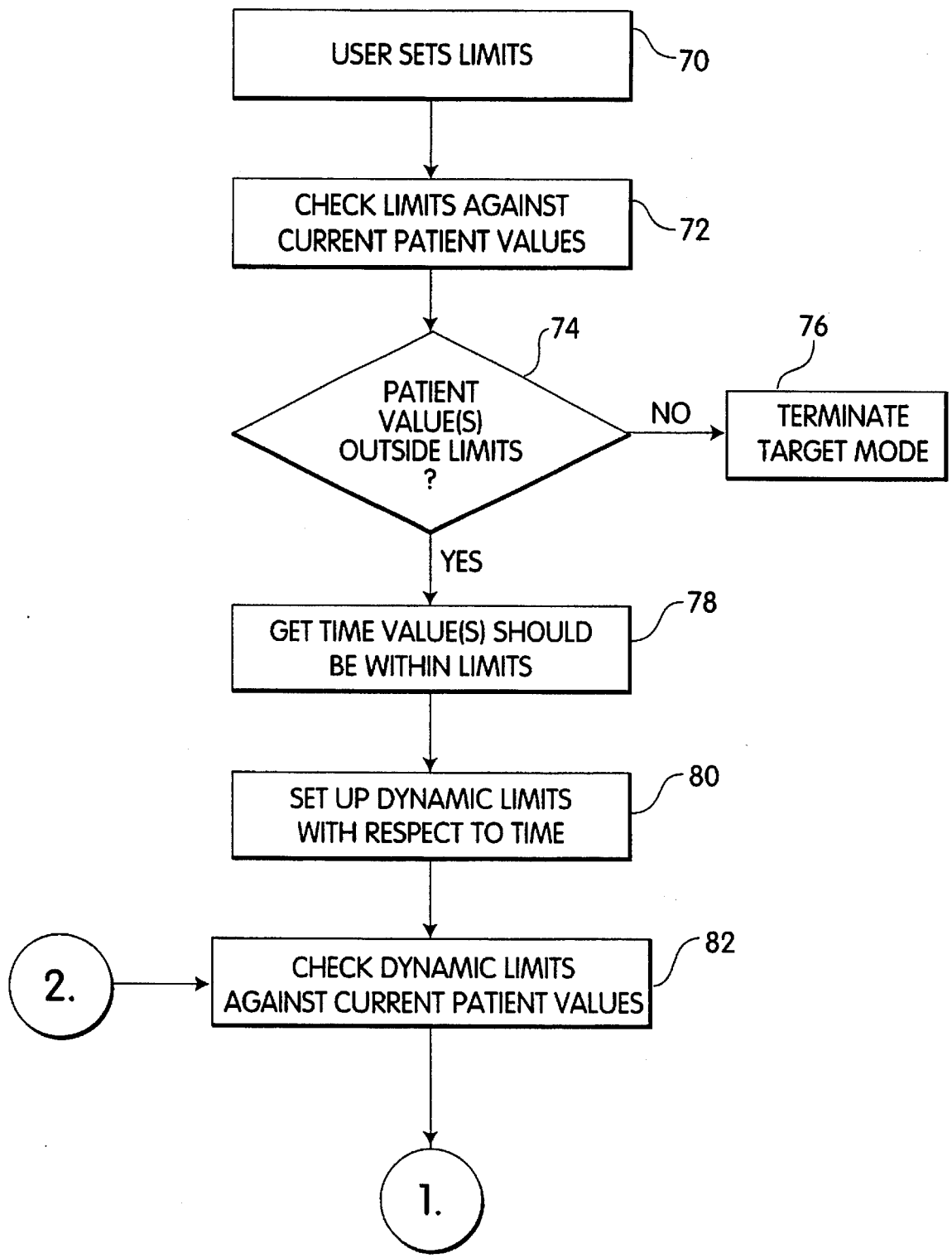
FIGS. 3A and 3B show a flow diagram of a method for detecting an alarm using a target mode in accordance with the present invention.
Figure 3B:
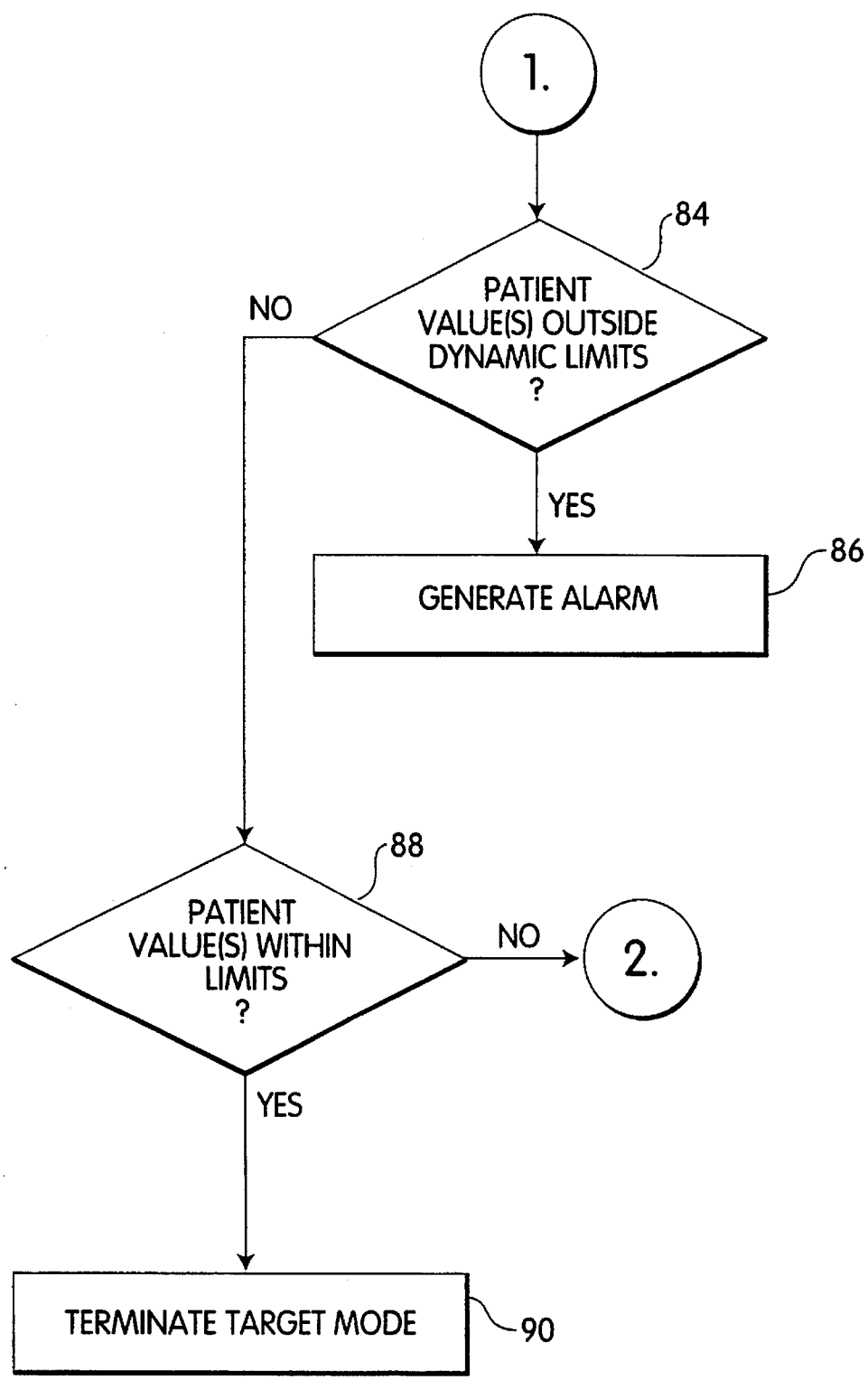

A flow diagram of the alarm detection technique of the present invention using target mode is shown in FIGS. 3A and 3B. In a preferred embodiment, the alarm detection technique of the invention is implemented as a software program which is executed on system processor 20 (FIG. 1). The invention can, for example, be implemented in the C/C++ programming language.

A user sets target limits of the physiological parameter in step 70. The target limits are based on the expected steady state range of parameter values after the intervention procedure. Target limits can be set for each physiological parameter that is expected to change as a result of the intervention. The setting of the target limits in step 70 initiates the target mode. In step 72, current measured parameter values are checked against the target limits. When the measured values are determined to be within the target limits in step 74, the target mode is terminated in step 76. When the current measured values are outside the target limits, the required time for the physiological parameter to be within the target limits is obtained in step 78. The required time can be preprogrammed for particular procedures and stored in memory 22 or can be selected by the user through operator interface 28. Next, the dynamic limits are established in step 80 based on the required time, the target limits and the current value of the physiological parameter. As discussed above, the dynamic limits can be established immediately when the user selects the target limits or can be delayed until the user indicates to the system that the intervention procedure is beginning.

In step 82, each measured parameter value is checked against the dynamic limits. When any of the measured values is outside the dynamic limits, as determined in step 84, an alarm is generated in step 86. The alarm corresponds to the conditions represented by curves 56 and 58 in FIG. 2. When the measured value is determined to be within the dynamic limits in step 84, the measured value is compared with the target limits in step 88. When the measured value is determined in step 88 to be within the target limits, the target mode is terminated in step 90. Thereafter, an alarm is generated if the measured parameter value goes outside the target limits. When the measured parameter value is determined in step 88 to be outside the target limits, the procedure returns to step 82 to check the next measured parameter value against the dynamic limits. Thus, if the measured values remain within the dynamic limits, no alarm is generated. The measured values eventually fall within the target limits and the target mode is terminated in step 90.

While there have been shown and described what are at the present considered the preferred embodiments of the present invention, it will be obvious to those skilled in the art that various changes and modifications may be made therein without departing from the scope of the invention as defined by the appended claims.

What is claimed is:

1. A patient monitoring system comprising: a sensor for measuring values of a physiological parameter; and a processor coupled to said sensor for processing said measured parameter values measured by said sensor, said processor comprising:

means for setting target limits of the physiological parameter in response to user selections;

means for initiating a target mode after setting of said target limits;

means for calculating time-varying dynamic limits based on the current value of the physiological parameter and on the target limits of the physiological parameter;

means for comparing said measured parameter values with said dynamic limits in said target mode; and means for generating an alarm when any of said measured parameter values falls outside said dynamic limits.

2. A patient monitoring system as defined in claim 1 wherein said processor further includes means for terminating said target mode when any of said measured parameter values falls within said target limits.

3. A patient monitoring system as defined in claim 2 further including a display unit, said processor further including means for indicating on said display unit that said target mode has terminated.

4. A patient monitoring system as defined in claim 2 wherein said processor further includes means for generating an alarm when any of said measured parameter values falls outside said target limits after said target mode has been terminated.

5. A patient monitoring system as defined in claim 1 wherein said means for calculating dynamic limits includes means for initiating said dynamic limits at a time when an intervention procedure is beginning.

6. A patient monitoring system as defined in claim 1 wherein said processor further includes means responsive to a user request for reinitiating said target mode after an alarm is generated.

7. A patient monitoring system as defined in claim 1 wherein said means for calculating dynamic limits includes means for establishing dynamic limits that define an acceptable range of values of said physiological parameter during a transition between a current measured value and a value that falls within said target limits.

8. A patient monitoring system as defined in claim 1 wherein said means for calculating dynamic limits includes means for establishing upper and lower dynamic limits which include a current measured value of the physiological parameter between them and which intersect said target limits at a later time.

* * * * *